United States Patent
Grocela

(10) Patent No.: US 9,143,106 B1
(45) Date of Patent: Sep. 22, 2015

(54) METHOD, DEVICE AND SYSTEM FOR PROVIDING SPEECH

(71) Applicant: Grindstone Medical LLC, Boston, MA (US)

(72) Inventor: Joseph A. Grocela, Weston, MA (US)

(73) Assignee: Grindstone Medical LLC, Boston, MA (US)

( * ) Notice: Subject to any disclaimer, the term of this patent is extended or adjusted under 35 U.S.C. 154(b) by 125 days.

(21) Appl. No.: 14/142,269

(22) Filed: Dec. 27, 2013

Related U.S. Application Data

(60) Provisional application No. 61/747,344, filed on Dec. 30, 2012.

(51) Int. Cl.
*H03G 3/00* (2006.01)
*A61F 2/20* (2006.01)

(52) U.S. Cl.
CPC .... *H03G 3/00* (2013.01); *A61F 2/20* (2013.01)

(58) Field of Classification Search
None
See application file for complete search history.

(56) References Cited

U.S. PATENT DOCUMENTS

| | | | | |
|---|---|---|---|---|
| 2,273,077 A | * | 2/1942 | Wright | 472/64 |
| 3,766,318 A | | 10/1973 | Webb | |
| 3,914,550 A | | 10/1975 | Cardwell, Jr. | |
| 4,039,756 A | | 8/1977 | Burtschi | |
| 4,264,989 A | * | 5/1981 | Wiley | 623/9 |
| 4,489,440 A | | 12/1984 | Chaoui | |
| 4,538,607 A | | 9/1985 | Saul | |
| 4,550,427 A | | 10/1985 | Katz et al. | |
| 4,612,664 A | * | 9/1986 | Walsh et al. | 381/70 |
| 4,627,095 A | | 12/1986 | Thompson | |
| 4,633,864 A | * | 1/1987 | Walsh | 128/207.15 |
| 4,685,448 A | | 8/1987 | Shames et al. | |
| 4,691,360 A | | 9/1987 | Bloomfield, III | |

(Continued)

FOREIGN PATENT DOCUMENTS

| | | | | |
|---|---|---|---|---|
| DE | 3902950 A1 | | 10/1990 | |
| DE | 10302759 A1 | | 10/2003 | |
| JP | 11069476 A | * | 3/1999 | H04R 1/14 |

OTHER PUBLICATIONS

English machine translation of JP11-069476 (Imamura et al., Artificial Larynx for Helping Sound Production, published Mar. 1999).*

(Continued)

*Primary Examiner* — Wayne Young
*Assistant Examiner* — Mark Fischer
(74) *Attorney, Agent, or Firm* — Adler Pollock & Sheehan P.C.; Daniel J. Holmander, Esq.; George N. Charles, Esq.

(57) ABSTRACT

A device for providing speech to a user has a sound wave generator, a sound wave guide for guiding the sound wave to a user's nasal cavity, an airflow generator for producing airflow through the sound wave guide, a pitch controller, and a volume controller. The device causes air and sound waves to pass through the user's mouth so the user can convert the airflow and sound waves to speech. The device can have a nasal cover or nasal prongs to engage the nose. The resulting speech can be controlled to have a substantially constant volume, and can be controlled to have proper tonal inflection. The sound wave generator can provide more than one frequency at a time. The sound wave generator can be a musical instrument. The device is handheld and portable. The device can be used to train a user to control a singing voice.

15 Claims, 6 Drawing Sheets

(56) References Cited

U.S. PATENT DOCUMENTS

| | | | |
|---|---|---|---|
| 4,706,292 A | | 11/1987 | Torgeson |
| 4,821,326 A | | 4/1989 | MacLeod |
| 5,326,349 A | | 7/1994 | Baraff |
| 5,828,758 A | * | 10/1998 | Byce et al. ............ 381/70 |
| 6,724,898 B1 | * | 4/2004 | Frankle ............ 381/70 |
| 6,735,315 B1 | | 5/2004 | Ifukube et al. |
| 2003/0031326 A1 | | 2/2003 | Lukacovic |
| 2013/0018462 A1 | | 1/2013 | Huang |

OTHER PUBLICATIONS

Liu, H., Ng, M. L., "Electrolarynx in voice rehabilitation", Auris Nasus Larynx 34 (2007) 327-332, Elsevier.

Moffett, B., Pindzola, R, "Acoustic Properties of Artificial Larynx Speech", NSSLHA 1988.

"Ultra Voice", www.ultravoice.com, http://www.ultravoice.com/how.htm (Accessed May 10, 2013).

"New Artificial Larynx Does Away With Dreaded 'Robot Voice'" www.popsci.com, http://www.popsci.com/technology/article/2009-12/new-artificial-larynx-does-away-dreaded-robot-voice (Accessed May 10, 2013).

"TruTone Electronic Speech Aid" www.griffinlab.com, http://www.griffinlab.com/Products/TruTone-Electrolarynx.html (Accessed May 10, 2013).

\* cited by examiner

METHOD, DEVICE AND SYSTEM FOR PROVIDING SPEECH

BACKGROUND AND SUMMARY OF THE INVENTION

People who have had a laryngectomy, or removal of the vocal cords for various reasons, are either unable to phonate, or make sounds. Current techniques that these people may use to communicate verbally include "burp talking" by swallowing air, using a vibrational device placed over their neck while moving their lips, or using a reed-like device in a "talking tracheostomy" to make sounds.

"Burp talking" is somewhat effective, but is out of range of normal human speech frequencies, monotonal, and likely perceived as unhygienic and rude. It is exhausting to the patient, as well as socially isolating.

Using a vibrational device on the neck produces robotic, monotonal sounds, which do not convey tonal inflection of the voice. As an example of this, when asking the question "Are you going to the store?" a speaker is likely to have a higher pitch of his voice at "store" than "are." However, speakers from some countries, such as Ireland, might say "are" with a higher pitch than "store."

Although an individual may wish to engage such a person in conversation, and although such a person may have a very mild Irish accent from spending a substantial amount of time in the USA, the individual may have a good deal of trouble understanding such a person. It may be necessary for the foreigner to repeat many things because her pitch for speech follows the above patterns. She may ask the individual a question, and the individual may not know to respond because it takes time to process the fact that she is not making a statement.

The human voice has multiple tones, even when one may sing a precise note. Each of these tones allows the National Security Agency (NSA) to identify an individual speaking, even if they try to disguise their voice. Other sounds comprise overtones. A precise tuning note of the First Violin Seat to tune the orchestra actually consists of about 60 overtones, which allows you to recognize it as such and distinguish this from another instrument such as a flute. This is why the single-tone vibrational device sounds far from a human voice.

The vibrational device also does not allow the same volume of many letter sounds as the remainder of the speech. If the vibrational device is softer than the sounds "CH," "F," "H," "K," "P," "Q," "T," "5," and "X," one will only hear these sounds, making communication very difficult. If the person has a tracheostomy, and is unable to pass air out of his or her mouth, then the above will be louder, once again, making communication very difficult.

On the other hand, if the person has a tracheostomy, and is unable to pass air out of his or her mouth, then the above sounds will be silent, and the rest of the speech will be louder, once again, making communication very difficult.

People with reed-like "talking" tracheostomies can get monotonal sounds, but without inflection. If one can move air, they can make the letter sounds above, but with likely volume mismatch.

For example, "Cheese" may sounds as "CH . . . SS" with the person who can pass air out of their mouth, but with non-functioning vocal cords. "Cheese" may sound as "chEEs" in someone who uses a vibrational device, and cannot pass air out of their mouth. "Cheese" may sound as either through a "talking" tracheostomy.

There is also a need for a speech providing device for individuals who are capable of normal speech. Some people are just not musically inclined, or "tone deaf." It is possible that these people can get a better grasp of tone through feel, rather than by hearing.

In an opera, the soprano belts out beautiful but very loud notes. The lower pitched contra alto sings quietly in the background. The tenor steals the show in Pucchini, yet the sinister bass makes the audience turn their good ear towards the stage. In a brass band, the trumpets with their high pitches can hold long notes, but the baritones for only a few seconds. They do not even offer the tuba for many bands, but allow fourth graders to play the larger bass fiddle in orchestra. This is because the lower pitch tones require larger amounts of air to create them, whether in the human "voice box" or the brass instrument.

The instant invention relates to devices for providing speech to users and for improving a user's ability to speak and sing.

The instant invention provides a device and a method that introduce a sound wave into the user's nasal cavity so the user can convert the sound wave into speech using the user's mouth.

The device includes a sound wave generator that a user can turn on to produce a sound wave. A sound wave guide is dimensioned and configured to extend between a first end that is adjacent to the sound wave generator and the second end that is configured to be adjacent a user's body, in particular the user's nasal cavity or nostrils. An airflow generator produces airflow through the sound wave guide from the first end to the second end at the user's nasal cavity. A pitch controller allows the user to modify the pitch of the sound wave, and a volume controller allows the user to modify the volume of the sound wave. Thus, the device moves air and sound waves through the sound wave guide, into the user's nasal cavity, and into the user's mouth, where the user can convert the air and sound waves to speech by moving his or her mouth.

The second end of the sound wave guide can be in the shape of a nasal cover, such as one that is typically used with a (continuous positive airway pressure) CPAP machine. Alternatively, it can be a pair of nasal prongs, each nasal prong being configured to engage one of the user's nostrils.

The device includes a volume controller and a pitch controller. The user can speak at a substantially constant volume by properly controlling the volume of the sound wave provided to the user. The pitch controller of the device adjusts the pitch of the sound wave so the resulting speech has the desired tonal inflection. The sound wave pitch controller and volume controller can be programmed to provide a predetermined pitch pattern of the sound wave and a predetermined volume pattern of the sound wave.

In one embodiment, the sound wave generator is a brass instrument, and the sound wave guide is a funnel. This allows a user to speak or sing with a voice that sounds like the instrument providing the sound wave to the user.

To provide the user with a more human-like voice, the sound wave generator provides more than one frequency at a time.

The airflow generator can be a fan or another mechanism for propelling air. In some embodiments, the airflow generator is a fan or a compressed air supply.

Preferably, the device is dimensioned and configured to be held in one hand or both hands of the user so that it is comfortable to use and easily portable.

The present invention also teaches a method for providing speech to a user using the device of the present invention. The method includes the steps of providing a sound wave generator, actuating the sound wave generator to generate a sound wave, controlling the pitch and volume of the sound wave, and guiding the sound wave to a user's nasal cavity, thereby causing the sound wave to pass through the user's mouth, so it can be converted to speech by the user.

Guiding the sound wave to the user's nasal cavity can include the step of providing a sound wave guide. The sound wave guide also guides air from a fan that can be actuated to push air towards the user's nasal cavity.

To allow the user to speak with proper inflection, the pitch of the sound wave can be changed in the middle of a user's speech, including in the middle of a sentence, or in the middle of a word.

The present invention allows the user to be more easily understood because the method of the present invention can be used to produce speech that has a substantially constant volume level throughout.

In some embodiments, the method of the present invention can be used to control the tone and the frequency of the speech. This is useful for controlling the meaning of a word spoken by the user where a single word can have various meanings depending on the tone or inflection.

In some embodiments, the method uses a musical instrument to generate the sound wave, so that the user is capable of producing speech that sounds like the musical instrument.

The method can be used to train a user to sing a note by providing a sound wave with a desired target note, instructing the user to attempt to sing the same target note, and instructing the user to identify a standing wave that results when the user sings a note other than the target note.

Accordingly, among the objects of the instant invention are: the provision of a device and method for providing speech to users who lack vocal cords or cannot direct air through their mouth. Another object of the present invention is to provide a device and method for providing a human-like voice, rather than a monotone voice. Another object of the present invention is the provision of a device and method for teaching an individual to sing at desired notes. Another object of the present invention is the provision of a device and method for providing speech having a substantially constant volume. Another object of the present invention is the provision of a device and method for controlling the pitch of speech.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated of carrying out the present invention.

DESCRIPTION OF THE PREFERRED EMBODIMENT

Figure 1:
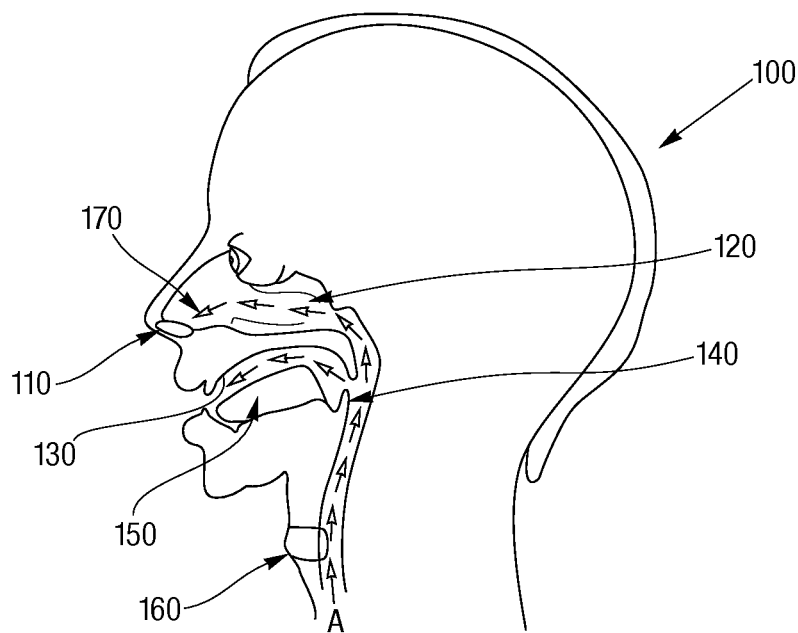
FIG. 1 is a sagittal view of the head of an individual showing normal speech.

Referring now to the drawings, the device for providing speech of the instant invention is illustrated and generally indicated at 10 in FIGS. 1-10. As will hereinafter be more fully described, the instant device provides natural-sounding speech to users and can be used to improve voice control in other users.

The device and method of the present invention provide human-like speech to users who otherwise are unable to speak normally, and provides a sound source for users wishing to modify their voice.

The device of the present invention has a sound wave generator that the user can turn on to generate a sound wave, and can turn off when the device is not in use. To improve social acceptance, the device is preferably configured and dimensioned to be handheld by the user. The device is portable, and easily activated and deactivated.

The device has a sound wave guide (or tube) that is dimensioned and configured to extend between a first open end that receives sound from the sound wave generator and a second open end that delivers sound to the user, typically at the user's nasal cavity. The second end of the sound wave guide can be configured to engage the user's nose by way of a pair of nasal prongs or a nasal cover that is typically used in CPAP machines. The engagement method can be selected according to user preferences. The sound waves are thus directed from the sound wave generator, to the user's nasal cavity, and then to the user's mouth, where the user can convert the sound waves to speech.

The device also has an airflow generator for producing airflow through the sound wave guide from the first end to the second end, and thus to the user's nasal cavity. The user can manipulate the airflow with the user's mouth to form sounds.

The device includes a pitch controller and a volume controller for the sound wave generator, so the user can control the device to provide a desired sound wave.

The device adjusts the volume and the pitch of the sound wave to provide a human-like sound in the resulting speech that exits the user's mouth. Controlling the sound wave allows the user's speech to have human-like tones and substantially constant volume.

These controllers can be preprogrammed to provide a predetermined pitch pattern of the sound wave and a predetermined volume pattern of the sound wave. Alternatively, the user can control the pitch and volume by way of a manual lever and/or button on the device.

The sound wave generator can be an electronic speaker, a musical instrument, or another sound source. An electrically powered sound wave generator or another sound source that can provide human-like sound waves may be desirable for a user wishing for the device to provide a human-like voice to the user. A musical instrument is a desirable sound wave source for a user wishing to have a voice that sounds like a musical instrument. The sound wave generator preferably provides sound of more than one frequency at a time to a user.

The sound wave may be guided to the user in various ways. For example, a sound wave guide in the shape of a funnel may be used. A straight tube may be used in other embodiments. Still other shapes are possible without departing from the scope of the present invention. The sound wave guide of the device allows the device to push air and sound through the user's nasal cavity and mouth. This airflow is provided by an airflow generator, such as a fan or a compressed air supply, or another mechanism.

The present invention also provides a method for providing speech to the user. The method includes the steps of providing a sound wave generator and activating the sound wave generator to generate a sound wave. The pitch and volume of the sound wave are controlled to provide the desired sounds. The sound wave is guided to the user, typically a user's nasal cavity. The sound is caused to travel through the user's nasal cavity and into the user's mouth, where the user can convert the sound wave to speech using the user's lips, teeth, and tongue, as in normal human speech.

The method also includes guiding the sound wave to the user's nasal cavity, for example, by the structure discussed herein. The method also includes providing air to the user, from a fan, a compressed air source, or another similar mechanism.

The user can control the pitch and volume of the sound wave at any time, including during speech. This is desirable when the user is asking a question or otherwise changing the tone or pitch of a word to change the meaning of that word.

The user can adjust the airflow and the volume of the sound wave provided to the user so the user's speech has a substantially constant volume.

The present invention provides a training method for training a user to sing a note by setting the sound source to the desired note, instructing the user to sing the desired note, and instructing the user to listen for a standing wave that results when the user is singing the wrong note.

FIG. 1 shows a sagittal view of the head 100 of an individual showing normal speech. FIG. 1 shows the individual's nose 110, sinuses 120, mouth 130, epiglottis 140, tongue 150, and vocal cords 160. FIG. 1 shows how air is directed upwardly over the vocal cords, in the direction of the arrows A. Air moves through vibrating vocal cords 160, comes out mouth and nose as sound 170 is phonated by tongue and mouth.

Figure 2:
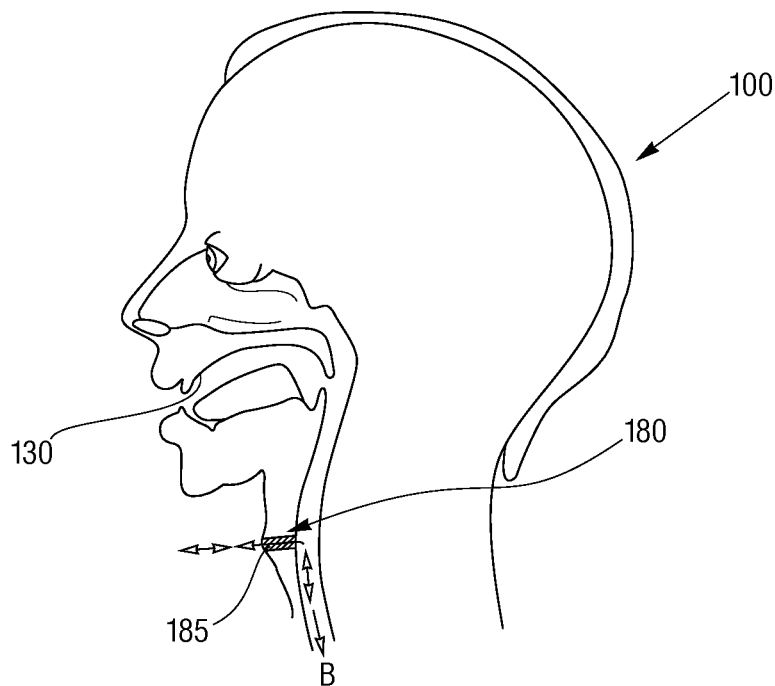
FIG. 2 is a sagittal view of the head of tracheostomy patient, showing air flow.

FIG. 2 shows a sagittal view of the head of tracheostomy patient. During breathing, air moves in and out of the tracheostomy tube 185. The individual's vocal cords may be removed from the vocal cord area 180. Thus, air does not pass over the vocal cords, as shown by the airflow arrows B in FIG. 2. Also, it does not pass through the individual's mouth 130.

Figure 3:
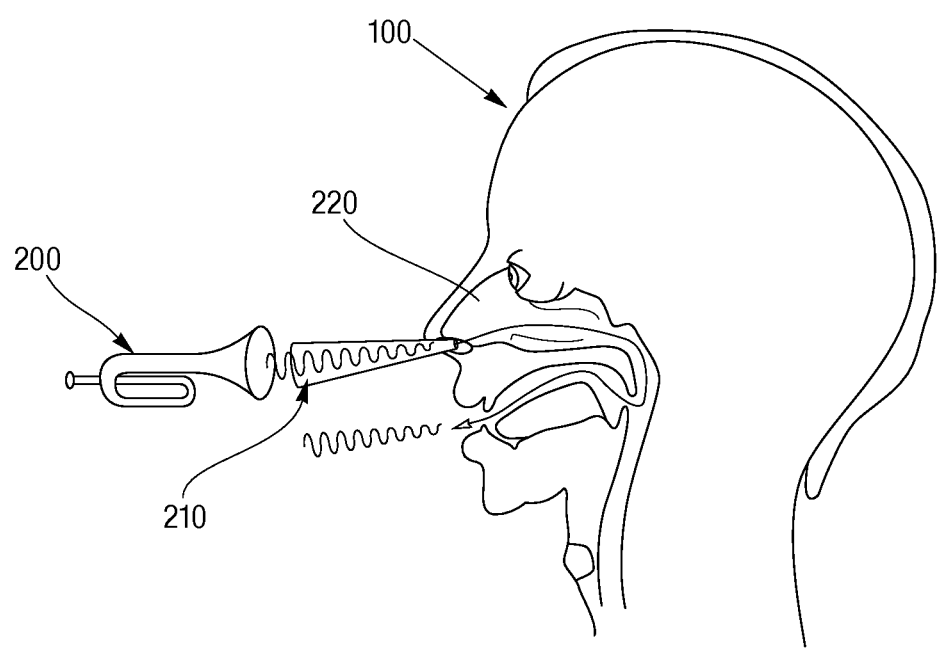
FIG. 3 is the sagittal view of the head of a user, with an instrument providing sound waves to the nasal cavity of the user.

FIG. 3 shows a sagittal view of the head 100 of a user, with a first embodiment of the present invention in which an instrument 200 provides sound waves 210 to the nasal cavity 220 of the user. The instrument 200 at the left directs sound waves into a first end of a funnel. The second end of the funnel is connected to the user's nose, so that the sound waves are directed into the user's nostrils. The air and sound waves travel from the nasal cavity into the mouth, where it can be converted by the user to speech.

A person generates both vibrational sound and airflow from a brass instrument, which is in this case a baritone. The sound waves and air flow down a funnel and into the nostrils of the patient/subject. The air flows so that the user can make the sounds "ch," "f," "h," "k," "p," "q," "t," "s," and "x." The volume of the hard consonants and vowels is equal or nearly equal, and avoids "dropout" of sounds during words such as "cheese," as discussed above.

Using the present invention, the tone or pitch may be changed to any frequency and volume, even during a word. The input may be monotonal and robot-sounding, but multiple frequencies may be input at the same time, allowing a single source for multiple frequencies.

Implementation of multiple tones allows for singing and multiple harmonies. The Andrews Sisters, identical triplet singers, had beautiful harmonies, likely from very similar vocal cord structure. This could theoretically be performed with the device.

Changing the tone during a sentence conveys meaning of that sentence better, and can avoid the cultural language mishaps discussed above.

China, the world's most populous country, with likely the world's largest smoker population, will likely have the most people with laryngectomies and tracheostomies. Mandarin and Cantonese, the main dialects of China, are impossible to speak without changing tones. The word "xu" means different things at different pitches. That's why these dialects sound "sing-song"-ish. This technology would be useful in China, because an individual could communicate effectively in China for the first time with this device.

Tone-deaf people could be trained to match tones input nasally by the device. If the person sings 1 Hz above the tone, there will be an interference wave generated once a second. 2 Hz=twice a second. If one generates no standing wave, they are spot-on, with their frequency. (Musicians use instruments like this.)

One could talk or sing as themselves, or use another voice or voices simultaneously. A user of this device could have the voice of a baritone euphonium, trumpet, violin, or other instruments or sounds. Limitless choices.

Figure 4:
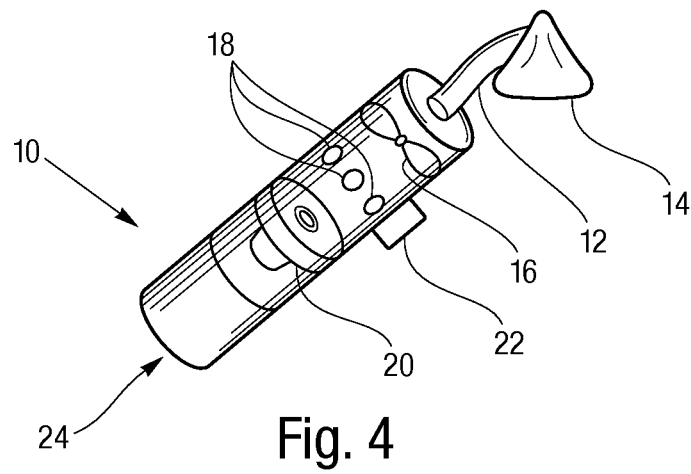
FIG. 4 is a first embodiment of the device of the present invention.

FIG. 4 is a first embodiment of the device 10 of the present invention, showing a portable device. The device is configured to be easily used by an individual. It is dimensioned and configured to be handheld. It has a sound wave guide in the form of a tube 12, the tube having a second end that is a nose cover 14 similar to that used on a CPAP machine. The tube 12 and nose cover 14 transmit air and sound from the device to the nasal cavity of the user. To advance air through the tube, the device has a fan 16 (an airflow generator) and air intake holes 18. An audio speaker 20 (sound wave generator) in the device produces the sound wave to be transmitted to the user's nasal cavity. The user can easily adjust a control button and/or lever 22 on the side of the device to change the pitch and the air flow. For example, sliding the lever up can increase the pitch/frequency, and sliding it down can decrease the pitch/frequency; and pushing the button in can provide more air flow. The device has a base that houses a battery for powering the components on the device. The base also supports electronics and a sound library. The device is roughly the size of a microphone for best social acceptance and compliance.

Figure 5:
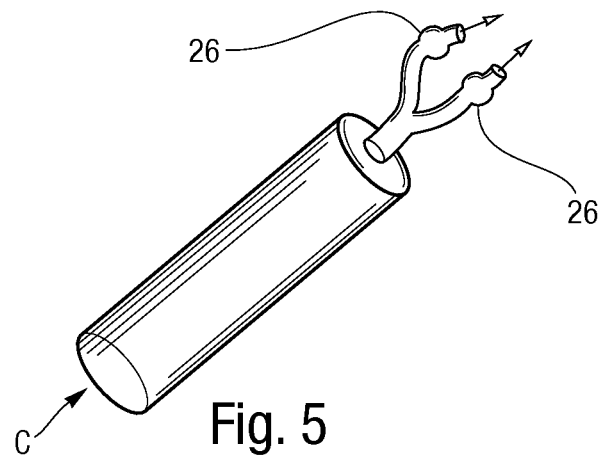
FIG. 5 is an embodiment of the nosepiece for the device of the present invention.

FIG. 5 is an embodiment of the nosepiece for the device of the present invention. This embodiment of the nosepiece has a pair of nasal prongs 26. Each nasal prong is configured to engage a nostril of the user. Like the embodiment of FIG. 4, the nasal prongs are connected to a tube that guides air and sound to the nasal cavity of the user in the direction of arrow C.

Figure 6:
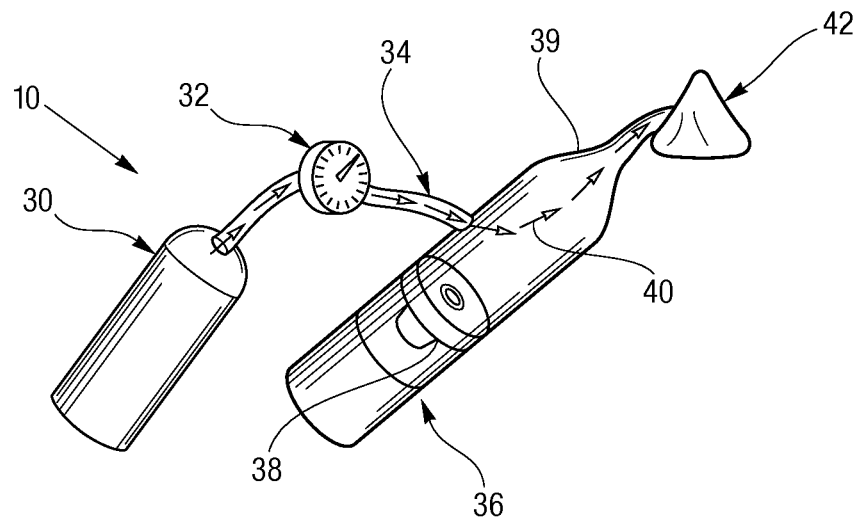
FIG. 6 is a second embodiment of the device of the present invention.

FIG. 6 is a second embodiment of the device of the present invention. In this embodiment, air is provided from a compressed air supply 30. A pressure gage and flow meter 32 allow for proper control of the airflow through the device 10. An outlet flow tube 34 directs air from the compressed air supply 30 towards a housing 36 containing a speaker 38. The speaker 38 produces a sound wave. The housing has a neck portion 39 that directs the sound wave and airflow 40 to a nose cover 42, similar to a CPAP nose cover.

Figure 7:
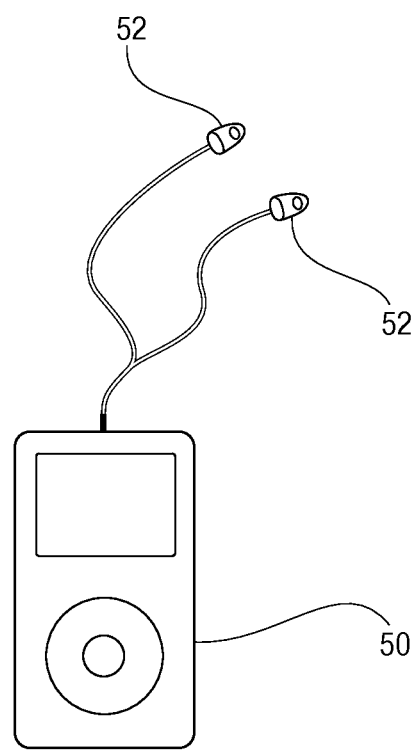
FIG. 7 is a third embodiment of the present invention.

FIG. 7 shows an embodiment for use with an individual who can supply air, such as an individual who is not a tracheostomy patient like the one shown in FIG. 2. This embodiment has a sound source 50 and a pair of nasal prongs 52. The nasal prongs 52 could be replaced with another structure capable of directing the sound wave directly to the mouth.

This embodiment allows for retrograde nasal source of any type of sound. In addition to a retrograde air supply with a nasal sound source, the air supply may be antegrade in the case of a user who is able to supply air.

The invention is useful for "mute" or aphonic patients. It provides sound and allows the user to change voice characteristics and tonal/frequency precision.

The device also increases the range of the user's voice. A user can speak or sing deeper and higher than normally possible.

The device is useful as a training device for singing, and useful for one person singing harmony.

Other users may enjoy singing with a voice that sounds like an instrument. The device allows a user to use the sound from as an inanimate source (singing as a violin, etc) or another person.

The device is particularly useful for providing air and sound waves to improve understanding of speech tone/frequency in colloquial language. For example, the device uses air and sound waves to allow a user to speak Cantonese or Mandarin dialects or other language that require tone/frequency changes for language with identical words spoken at higher/lower tones/frequencies.

The device can take on various forms. The device can be portable and handheld, or it can be larger and connected to a fixed sound source. The device can be configured to provide an external air supply to the user, or it can take advantage of the user's own air supply. The device can have a single nose cover, or it can be fitted with individual nasal prongs.

Figure 8A:
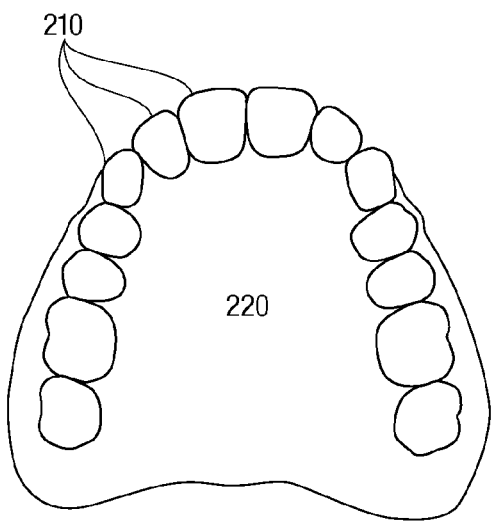
FIG. 8A is a view of the upper teeth and hard palate of an individual.
Figure 8B:
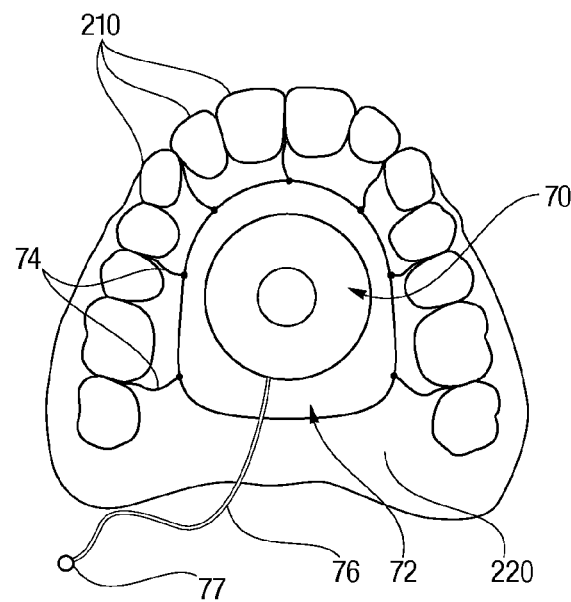
FIG. 8B is a view thereof with a speaker secured inside the mouth.

FIGS. 8A-10 show an embodiment in which a speaker mounted within the user's mouth provides a sound wave. FIG. 8A shows the upper teeth 210 of the individual 200, with the hard palate 220 between the teeth. FIG. 8B shows the speaker 70 mounted so that it is in facing relation with the upper palate 220. The speaker 70 is held in place on a base 72 similar to a dental retainer, which is held in place by holding clips and wire 74 similar to that used on a typical dental retainer. An electrical wire 76 can extend from the speaker and out of the user's mouth. The wire terminates in an end 77 that can engage a driver or a power source, so the speaker can be connected to a driver or a power source.

Figure 9:
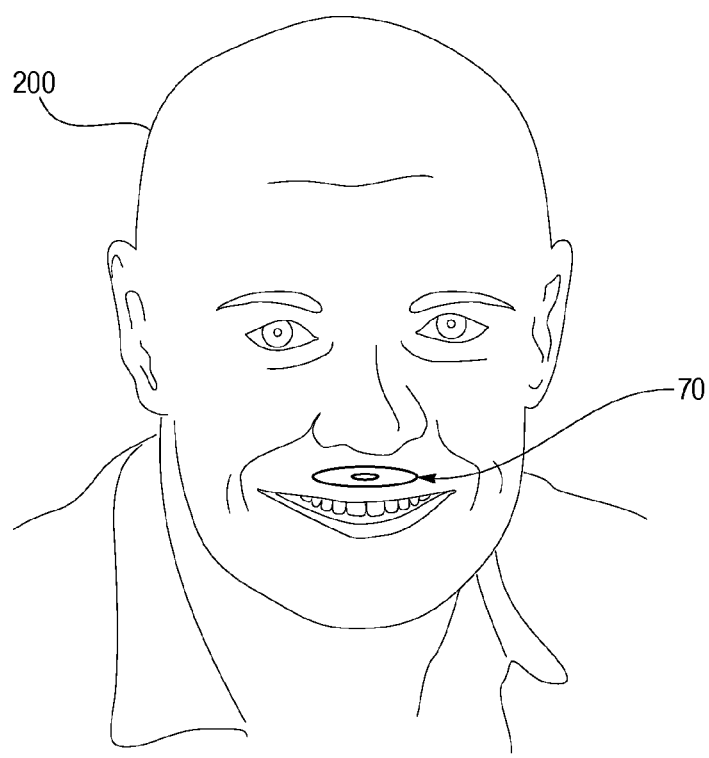
FIG. 9 is a front view of the user, showing the placement of the speaker.
Figure 10:
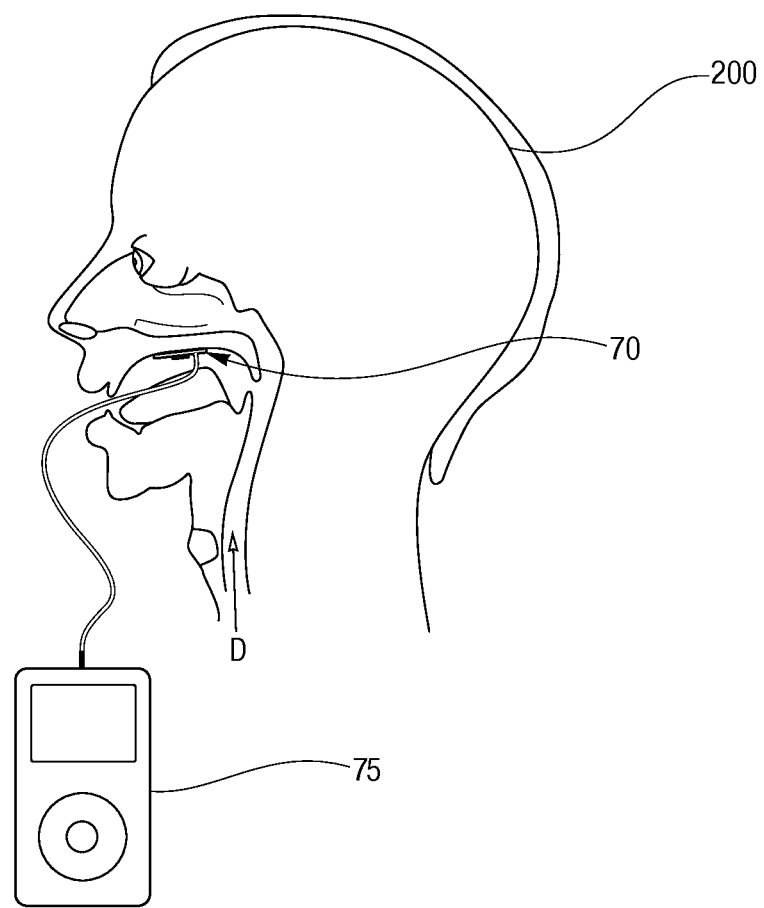
FIG. 10 is a sagittal view thereof.

FIG. 9 shows a front view of a user's head, indicating where the speaker 70 is seated. The speaker is hidden within the user's head when the user's mouth is closed, but FIG. 9 shows the relative location of the speaker 70 in the user's mouth. FIG. 10 shows a sagittal view of the user 200 with the speaker mounted in the retainer-like base on the roof of the user's mouth. The speaker is seated so that it allows sound and air to pass by the speaker within the user's mouth. The speaker is connected to a driver/power source 75 for controlling the sound emitted from the speaker. The user pushes air in the direction of arrow D, as in normal speaking or singing. The user modifies the airflow and sound as in normal speech and singing.

A cutoff switch (not shown) can be controlled by the user's tongue to silence the speaker while the user's mouth is closed.

It can therefore be seen that the present invention provides a device and method for providing speech to users who lack vocal cords or cannot direct air through their mouth. The present invention also provides a device and method for providing a human-like voice, rather than a monotone voice. The present invention also provides a device and method for teaching an individual to sing at desired notes. The present invention also provides a device and method for providing speech having a substantially constant volume. The present invention also provides a device and method for controlling the pitch of speech. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A device for providing speech to a user, the device comprising:
   a sound wave generator being selectively operable to produce a sound wave;
   a sound wave guide dimensioned and configured to extend between a first open end adjacent the sound wave generator and a second open end configured to be adjacent a user's body;
   an airflow generator for producing an airflow through the sound wave guide from the first end to the second end;
   a pitch controller to modify the pitch of the sound wave; and
   a volume controller to modify the volume of the sound wave;
   whereby the sound waves are capable of being caused to pass through the user's mouth, and the sound waves are capable of being converted to speech by the user;
   wherein the sound wave pitch controller and volume controller are programmed to provide a predetermined pitch pattern of the sound wave and a predetermined volume pattern of the sound wave.

2. The device of claim 1, wherein the second end of the sound wave guide is configured to engage a user's nose, the second end being in the shape of one of a nasal cover and a pair of nasal prongs.

3. The device of claim 1, wherein the volume controller adjusts the volume of the sound wave so that the resulting speech has a substantially constant volume.

4. The device of claim 1, wherein the pitch controller adjusts the pitch of the sound wave so the resulting speech has tonal inflection.

5. The device of claim 1, wherein the sound wave generator is a brass instrument.

6. The device of claim 5, wherein the sound wave guide is one of a funnel and a substantially cylindrical tube.

7. The device of claim 1, wherein the sound wave generator provides more than one frequency at a time.

8. The device of claim 1, wherein the airflow generator is one of a fan and a compressed air supply.

9. The device of claim 1, wherein the device is dimensioned and configured to be held in a hand of the user.

10. A method for providing speech to a user, the method comprising:
    providing a sound wave generator;
    actuating the sound wave generator to generate a sound wave, the sound wave having a pitch and a volume;
    controlling the pitch of the sound wave;
    controlling the volume of the sound wave;
    guiding the sound wave to a user's nasal cavity;
    causing the sound wave to pass from the user's nasal cavity and through the user's mouth, so it can be converted to speech by the user; and training the user to sing a note by instructing the user to identify a standing wave that results when the user produces a note other than a target note, wherein the step of actuating the sound wave generator further comprises generating the target note from the sound wave generator.

11. The method of claim 10, wherein the step of guiding the sound wave further comprises:

providing a sound wave guide having a first open end and a second open end, the first end being adjacent the sound wave generator and the second end being capable of being adjacent a user's body; providing a fan; and powering the fan to push air from a first end of a funnel in the direction of a second end of the funnel.

12. The method of claim 10, wherein controlling the pitch of the sound wave comprises the step of changing the pitch of the sound wave in the middle of speech, the speech being in the form of one of a sentence and a word.

13. The method of claim 10, wherein the user produces speech that has a substantially constant volume level throughout.

14. The method of claim 10, further comprising the step of controlling the tone and the frequency of the speech to control the meaning of a word spoken by the user.

15. The method of claim 10, wherein the sound wave generator is a musical instrument, so that the user is capable of producing speech that sounds like the musical instrument.

\* \* \* \* \*